United States Patent

Galiana et al.

Patent Number: 6,091,334
Date of Patent: Jul. 18, 2000

[54] DROWSINESS/ALERTNESS MONITOR

[75] Inventors: Henrietta L. Galiana, St. Lambert, Canada; Ian W. Hunter; Lynette A. Jones, both of Lincoln, Mass.; James L. Tangorra, Boston, Mass.

[73] Assignee: Massachusetts Institute of Technology, Cambridge, Mass.

[21] Appl. No.: 09/146,828

[22] Filed: Sep. 4, 1998

Related U.S. Application Data

[60] Provisional application No. 60/058,103, Sep. 5, 1998.

[51] Int. Cl.$^7$ .................................................. G08B 21/00
[52] U.S. Cl. ...................... 340/576; 340/439; 340/573.1; 340/575; 128/745; 351/209
[58] Field of Search ................................ 340/439, 573.1, 340/575, 576; 128/745, 733; 351/205, 209; 382/115, 181

[56] References Cited

U.S. PATENT DOCUMENTS

| | | | |
|---|---|---|---|
| 4,836,219 | 6/1989 | hobson et al. | 340/575 |
| 5,293,427 | 3/1994 | Ueno et al. | 382/1 |
| 5,570,698 | 11/1996 | Liang et al. | 128/745 |
| 5,573,006 | 11/1996 | Shimotani et al. | 340/575 |
| 5,583,590 | 12/1996 | Clupper | 340/573 |
| 5,689,241 | 11/1997 | Clarke, Sr. et al. | 340/575 |
| 5,729,619 | 3/1998 | Puma | 382/115 |
| 5,859,686 | 1/1999 | Aboutalib et al. | 351/209 |

FOREIGN PATENT DOCUMENTS

| | | |
|---|---|---|
| 196 13 614 A1 | 11/1996 | Germany. |
| 2 215 040 | 9/1989 | United Kingdom. |

OTHER PUBLICATIONS

Ueno et al., "Development of Drowsiness Detection System", Proceedings of the Vehicle Navigation and Information Systems Conference, Yokohama, Aug. 31–Sep. 2, 1994, pp. 15–20.

*Primary Examiner*—Daniel J. Wu
*Attorney, Agent, or Firm*—Bromberg & Sunstein LLP

[57] ABSTRACT

A method and apparatus for analyzing drowsiness of a subject. The monitor measures motion of the head of the subject and of one or both eyes of the subject in at least one dimension and derives at least one physiological indication such as gaze stability, saccade speed, saccade frequency, blink duration, and instrument-world scanning performance of the subject. The physiological indicator or indicators are compared with predetermined ranges of acceptable values in such a manner as to determine an onset of drowsiness in the subject.

5 Claims, 1 Drawing Sheet

DROWSINESS/ALERTNESS MONITOR

The present application claims priority from U.S. Provisional application Ser. No. 60/058,103 filed Sep. 5, 1998, which application is herein incorporated by reference.

TECHNICAL FIELD

The present invention pertains to a method and apparatus for monitoring alertness of a subject on the basis of saccade frequency and other physiological measures and for providing an alarm in case of detected drowsiness.

BACKGROUND OF THE INVENTION

Alertness, even in the face of highly repetitive or monotonous tasks, may be essential for the safety of the operator of automated machinery and of other persons whose well-being and lives may depend of the constant attention of the operator. Accurate monitoring of alertness and the detection of drowsiness is therefore crucial in such human functions as air traffic control, nuclear power plant operation, etc. Prior methods of monitoring alertness have entailed electroencephalographic recording.

SUMMARY OF THE INVENTION

In accordance with a preferred embodiment of the invention, there is provided a method for detecting drowsiness of a subject. The method has the steps of monitoring motion of the head of the subject in at least one dimension, measuring motion of one or both eyes of the subject, deriving at least one physiological indicator based on motion of the head and eye or eyes, and comparing the derived physiological indicator or indicators with predetermined ranges of acceptable values in such a manner as to determine any onset of drowsiness in the subject.

In accordance with alternate embodiments of the invention, the physiological indicator is selected from the group of gaze stability, saccade speed, saccade frequency, blink duration, and instrument-world scanning performance. Additionally, one or more alarms may be triggered based on the onset of drowsiness for restoring alertness of the subject.

BRIEF DESCRIPTION OF THE DRAWING

The invention will more readily be understood by reference to the following description taken with the accompanying drawing which depicts a schematic diagram of an apparatus for monitoring the alertness of a subject, in accordance with a preferred embodiment of the present invention. The drawing is intended to provide a better understanding of the present invention, but is in no way intended to limit the scope of the invention.

DETAILED DESCRIPTION OF SPECIFIC EMBODIMENTS

Figure 1:
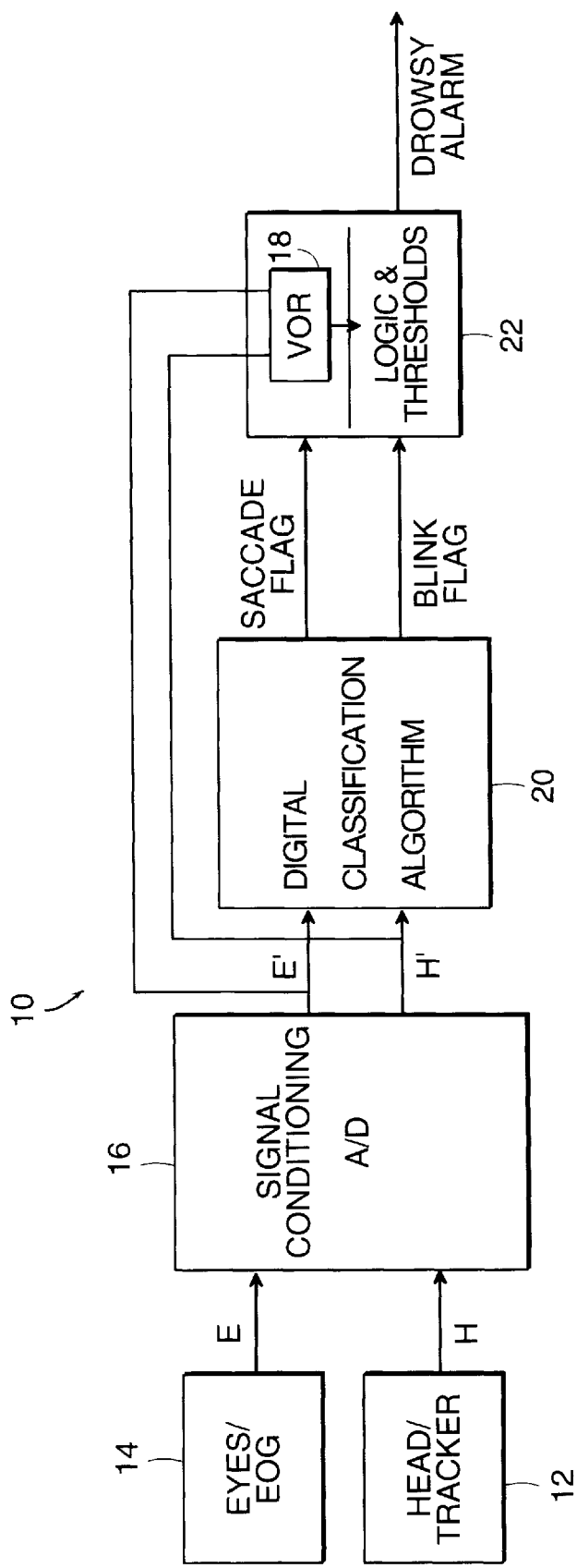

Studies of ocular reflexes have indicated that in the natural head-free condition, in which the position of the head of a subject is unconstrained, it is the quality of 'gaze' stabilization on targets in space, together with the speed of new target acquisition, that determine the quality of ocular reflexes. Gaze stability has the components of stability of the eye within the head and of the head in space. When the subject becomes drowsy, the gaze stability between saccades starts to drift, the number and peak speed of reorienting saccades decreases, and blink dynamics become very sluggish. Thus, in accordance with a preferred embodiment of the present invention, involuntary (reflex) characteristics such as those described may be monitored quantitatively in order to detect the onset of drowsiness. Eye and head movements are measured, allowing saccades, blinks, and an estimate of the gain of the vestibular-ocular reflex (VOR) to be derived. These data, in turn, may be linked to the scanning performance of the subject; for example, the relative dwell-time on various instruments or external targets, etc. The dwell time on such instruments or targets may, furthermore, be correlated with appropriate values based on the impact of the information provided by each to an alert subject. In a preferred embodiment, specified thresholds, and appropriate combinatorial logic is used to automate the alertness monitor and to trigger alarms, of a visual or non-visual nature, in accordance with the nature of the task being performed by the subject.

Many technologies are known for tracking head and eye movements and are within the scope of the present invention as described and as claimed in any appended claims. While examples are provided in the following discussion, all such equipment and methods are within the scope of the present invention as described herein and as claimed in any appended claims. Referring to FIG. 1, a schematic diagram is shown of an apparatus, designated generally by numeral 10, for monitoring the alertness of a subject, in accordance with a preferred embodiment of the present invention. A Head Tracker 12 tracks motion of the head of the subject in at least one dimension. Head Tracker 12 may be magnetically-based (Polhemus or Ascension), for example, or inertial-based (DC accelerometer, push-pull linear accelerometer, for example) tracker and may provide a single coordinate as a function of time. The head tracking sensor should have a bandwidth exceeding 20 Hz. Head Tracker 12 provides a signal H corresponding to the position of the head of the subject. Motion of the eyes of the subject is tracked by an Eye Tracker 14. In a preferred embodiment of the invention, eye tracking is performed using electrooculographic (EOG) or non-contact video-based eye trackers to provide binocular 2D trajectories. Eye Tracker 14 provides a signal E corresponding to the direction of regard of one or both of the eyes of the subject. In particular, eye angles may be measured and converted to electrical signals, with the eye angles referred, for example, to the nasal direction. Data streams E and H are digitized and prefiltered by signal conditioning unit 16, and are preferably recorded in memory and/or fixed in recording media. In either case, bandwidth exceeding 20 Hz is preferred. The digitized data stream corresponding to signals E and H are designated E' and H', respectively.

The head and eye position data are used by a VOR processor 18 to calculate the ideal conjugate VOR gain, taking into account the context, or, equivalently, the vergence, where the vergence set point is the sum of the two eye angles referenced to the nasal direction. The ideal or expected VOR may be referred to as the 'model' VOR. Since ocular responses in any protocol contain nystagmus, the signal analysis includes automatic classification of eye (or gaze) slow and fast phases, based, for example, on classification software described by Rey & Galiana, "Parametric classification of segments in ocular nystagmus," *IEEE Trans. Biomed. Eng.*, vol. 38, (1991), pp. 142–48, which is incorporated herein by reference. A U.S. Provisional patent application entitled "Automated Segmentation of Nystagmus or Other Complex Curves," and filed Feb. 18, 1998 is also incorporated herein by reference. Classification processor 20 sorts responses of the eyes into intervals corresponding to a slow phase and a fast phase (saccades), separately flagging blinks. Alarm processor 22 corrects for context (vergence) and evaluates gaze stability during the marked slow phases. Additionally, alarm processor 22 may calculate the fraction of time spent by the subject viewing targets in different sectors of the field of view of the subject. For example, if the subject is the operator of a vehicle such as a ground vehicle or an aircraft, the percentage of time spent by the operator viewing internal instruments and targets outside the vehicle may be calculated by processor 22. Alarm processor 22 applies specified thresholds and logical criteria, such as the conjunction of a first threshold with respect to a first criterion with a second threshold with respect to another criterion, in order to determine drowsiness in the subject. The criteria for determining drowsiness may include, without limitation, the calculated gaze stability of the subject, the speed and frequency of saccades, blink duration, and the performance of the subject in scanning instruments and the external environment.

The steps described above with respect to VOR processor 18, classification processor 20, and alarm processor 22 may be implemented on a single chip which may be integrated into head-mounted hardware. Processing may be performed in either analog or digital form, at each stage of the processing. In an alternative embodiment, the disclosed method for evaluating the drowsiness of a subject may be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Analysis of data obtained by performing the method described above is now discussed. Both eye movement (providing signal E) and head movement(providing signal H) are monitored in selected planes. With this information, it becomes possible to monitor gaze in space (E+H) which is the preferable variable for detecting the occurrence of saccades. Often, natural head turns can be associated with saccades or fast phases whose velocity with respect to the head is zero, while gaze velocity with respect to a fixed frame of reference is still in the range of saccades. The true neural determinant of saccade occurrence is the silencing of Pause cells in the brainstem and the release of activity on saccade-related Burst cells nearby. The speed of eye movements in the head is not a robust indicator; gaze in space is a preferred choice so long as the body is reasonably stationary in the environment in which the subject is operating.

Moreover, there is neurophysiological evidence that the rate of activation intervals on Burst cells decreases and is associated with noisy sustained backgrounds on pause cells as an animal nears a sleeping state. Hence, the measured saccadic rate, inasmuch as it is a measure of burst activation rate, provides an advantageous measure of drowsiness. In accordance with an alternate embodiment of the invention, this measure is complemented by estimates of VOR gain. While VOR gain is typically greater or equal to 0.6 while viewing targets in the far field, even in the dark, it is known that VOR gain may decrease significantly during drowsiness.

VOR gain and its correction for the current vergence set-point is discussed in Viire et al., A Reexamination of the Gain of the Vestibulo-Ocular Reflex, *Journal of, Neurophysiology*, vol. 56, pp. 439–450 (1986), and in Green & Galiana, Modelling on-line adaptation of the VOR gain with target distance and eccentricity, *Proc. 17th IEEE EMBC*, (IEEE, 1995), which is herein incorporated by reference.

In the present discussion, symbols represent the indicated variables, and sign conventions are as follows:

$E_R$, $E_L$: monocular horizontal eye angles (right, left), in degrees, with negative angles for nasal deviations;

$E_R+E_L$: the vergence angle, in degrees, subtended by the two lines of sight;

$E_R-E_L$: conjugate eye deviations, in degrees, with rightward with respect to the head defined as the positive sense;

$H_v$: horizontal head velocity, in deg-s$^{-1}$, positive is rightward as seen from above the head;

$Ev_{conj}$: conjugate eye velocity, in deg-s$^{-1}$, the time-derivative of $E_{Rl\ -EL}$;

R: distance in mm from center of head rotation to frontal plane containing the two eyes of the subject; and I: total interocular distance, center-to-center, in mm.

Since the VOR gain is a function of the depth of a target of interest, the two eyes are preferably monitored separately. As a result, the expected ideal conjugate VOR gain may be corrected for the current vergence set-point according to the approximate formula:

$$VOR_{ideal} = Ev_{conj}/H_v \approx -1 - R(E_R+E_L)(\cos E_R + \cos E_L)/(2I) \quad (1)$$

This is an approximation for the more complex relation between the required rotation of each eye for a given head perturbation, while fixating a visible target. The approximation replaces the dependence of eye angles on target distance and angular eccentricity with a dependency only on concurrent monocular eye angles.

As apparent to a person of ordinary skill in the art, the ideal gain when fixating at infinity is −1 (when vergence is zero), and quickly increases in magnitude with convergence angle. It is within the scope of the invention to apply calibration schemes to account for variability in head geometry across subjects.

During marked slow-phase segments, the goal of the visual-vestibular system is to maintain the stability on the retina of a selected target. While it is not necessary, within the scope of the invention, that the monitor have access to the selected visual goal, the monitor does have an indirect measure based on the monocular eye angels and the intersection of their lines of sight. For example, if a target is at optical infinity (relative to R and I), then the two eye angles will be identical, vergence is zero, and the ideal $VOR_{conj}$ gain is −1. In more general terms, $VOR_{ideal}$ (which is negative, from Eqn. 1) represents the appropriate gain for earth-fixed targets with measured vergence conditions. Gaze velocity is given by:

$$slip = GV = Ev_{conj} VOR_{ideal} * Hv \text{ (target earth-fixed)} \quad (2)$$

For the case of targets stationary in space (e.g., outside a vehicle), this also corresponds to the slip of targets on the retina (in degrees-$s^{-1}$), provided that the head tracker is inertial and measures the total head motion in space. Hence, visual acuity would require tighter limits on the levels of slip while viewing earth-fixed targets. In accordance with an embodiment of the invention, those time intervals where vergence angles clearly demark intervals while viewing targets inside the vehicle may be excluded form the slip threshold analysis. Alternatively, if tracking of the vehicle movement is also available, then Eqn. 2 may still be applied for body-fixed targets within the vehicle by replacing Hv with H'v=Hv-Pv, where Pv is the platform velocity, or:

$$slip = Ev_{conj} - VOR_{ideal} * H'v \text{ (target inside the vehicle)} \quad (3)$$

In the case of external but moving targets (such as another vehicle moving ahead at the same speed as the instant vehicle), decisions may be made by selecting the context (Eqn. 2 or 3) which provides the lowest slip level or by ignoring such 'noisy' intervals entirely, since a driver typically views either his instruments or the road marks most of the time.

The formulae cited above, based on-line eye deviations, may provide an ideal dynamic baseline against which to detect saccades and the performance of the conjugate VOR. In accordance with a particular embodiment of the present invention, an alarm flagging possible drowsiness results form processing the particular combination of reflex VOR performance (e.g., gaze stability), saccade rate, and, in some cases, blink frequency and/or duration. Recognition of a drowsiness state in terms of these variables or a subset thereof may be implemented, in accordance with an embodiment of the invention, using known techniques of non-linear processing including, for example, simple pattern detection with neural networks or other nonlinear filters.

The described embodiments of the invention are intended to be merely exemplary and numerous variations and modifications will be apparent to those skilled in the art. All such variations and modifications are intended to be within the scope of the present invention as defined in the appended claims.

We claim:

1. A method for analyzing drowsiness of a subject having a head and an eye, the method comprising:

a. measuring motion of the head of the subject in at least one dimension;

b. measuring motion of the eye of the subject;

c. deriving at least one physiological indicator of drowsiness in a waking subject, the at least one physiological indicator, selected from the group of saccade frequency, saccade speed, blink duration, blink frequency, instrument-world scanning performance, and gain of vestibular-ocular reflex, based on motion of the head and the eye; and d. comparing the at least one derived physiological indicator of the subject with predetermined ranges of acceptable values in such a manner as to determine an onset of drowsiness in the subject.

2. A method according to claim 1, further comprising:

e. triggering at least one alarm based the onset of drowsiness for restoring alertness of the subject.

3. A method for analyzing drowsiness of a subject having a head and two eyes, the method comprising:

a. measuring motion of the head of the subject in at least one dimension;

b. measuring motion of the eyes of the subject;

c. deriving at least one physiological indicator of drowsiness in a waking subject, the at least one physiological indicator, selected from the group of saccade frequency, saccade speed, blink duration, blink frequency, instrument-world scanning performance, and gain of vestibular-ocular reflex, based on motion of the head and the eyes; and d. comparing the at least one derived physiological indicator of the subject with predetermined ranges of acceptable values in such a manner as to determine an onset of drowsiness in the subject.

4. A drowsiness monitor for detecting drowsiness of a subject having a head and an eye, the drowsiness monitor comprising:

a. a head tracker for measuring motion of the head of the subject in at least one dimension;

b. an eye tracker for measuring motion of the eye of the subject; and c. an alarm processor for deriving at least one physiological indicator, the at least one physiological indicator drowsiness in a waking subject selected from the group of saccade frequency, saccade speed, blink duration, blink frequency, instrument-world scanning performance, and gain of vestibular-ocular reflex, based on motion of the head and eye, and comparing the at least one physiological indicator with predetermined ranges of acceptable values in such a manner as to determine an onset of drowsiness in the subject.

5. A drowsiness monitor according to claim 4, further comprising a classification processor for sorting responses of the eye of the subject according to intervals corresponding to a slow phase and a fast phase.

* * * * *